(12) United States Patent
McKay

(10) Patent No.: US 10,376,381 B2
(45) Date of Patent: Aug. 13, 2019

(54) INTERBODY BONE IMPLANT DEVICE

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 15/643,091

(22) Filed: Jul. 6, 2017

(65) Prior Publication Data

US 2017/0296357 A1    Oct. 19, 2017

Related U.S. Application Data

(63) Continuation of application No. 13/448,647, filed on Apr. 17, 2012, now Pat. No. 9,730,801.

(51) Int. Cl.
| | |
|---|---|
| *A61F 2/28* | (2006.01) |
| *A61F 2/30* | (2006.01) |
| *A61F 2/44* | (2006.01) |
| *A61F 2/46* | (2006.01) |
| *A61L 27/18* | (2006.01) |
| *C08L 71/00* | (2006.01) |

(52) U.S. Cl.
CPC .......... *A61F 2/4455* (2013.01); *A61L 27/18* (2013.01); *A61F 2/4611* (2013.01); *A61F 2002/2835* (2013.01); *A61F 2002/30059* (2013.01); *A61F 2002/30448* (2013.01); *A61F 2002/30784* (2013.01); *A61F 2002/30904* (2013.01); *A61L 2430/02* (2013.01)

(58) Field of Classification Search
USPC ............... 623/17.11–17.16, 21.18–21.19, 623/23.51–23.63; 606/61, 69, 91
See application file for complete search history.

(56) References Cited

U.S. PATENT DOCUMENTS

| | | | |
|---|---|---|---|
| 5,531,791 A | 7/1996 | Wolfinbarger, Jr. | |
| 6,863,673 B2* | 3/2005 | Gerbec et al. | ........... 606/99 |
| 7,498,041 B2 | 3/2009 | Masinaei et al. | |
| 7,815,682 B1 | 10/2010 | Peterson et al. | |
| 2002/0120338 A1 | 8/2002 | Boyer, II et al. | |
| 2003/0009235 A1 | 1/2003 | Manrique et al. | |
| 2003/0114936 A1 | 6/2003 | Sherwood et al. | |
| 2003/0167092 A1 | 9/2003 | Foley | |
| 2005/0021142 A1 | 1/2005 | Ganz et al. | |
| 2005/0085922 A1 | 4/2005 | Shappley et al. | |
| 2006/0233851 A1 | 10/2006 | Simon et al. | |
| 2006/0280803 A1 | 12/2006 | Kiumar et al. | |
| 2006/0293757 A1 | 12/2006 | McKay et al. | |
| 2007/0098756 A1 | 5/2007 | Behnam | |
| 2007/0233272 A1* | 10/2007 | Boyce et al. | ......... 623/23.63 |

(Continued)

*Primary Examiner* — Yashita Sharma

(57) ABSTRACT

A composite interbody bone implant device is provided including a body having a non-bone composition, such as a polymer, formed into a shape and including one or more cavities. An osteoinductive material, such as bone allograft tissue, may be retained in the one or more cavities of the body. The body is formable via injection molding and/or machining into a shape and size adapted for implantation at a surgical site. The dimensions of the body include a length, a width and a thickness, and the thickness of the body may be less than at least one of the length and width.

7 Claims, 6 Drawing Sheets

(56) References Cited

U.S. PATENT DOCUMENTS

| | | |
|---|---|---|
| 2008/0091270 A1* | 4/2008 | Miller et al. ............... 623/17.16 |
| 2008/0114465 A1 | 5/2008 | Zanella et al. |
| 2008/0281431 A1 | 11/2008 | Missos |
| 2009/0130173 A1 | 5/2009 | Behnam et al. |
| 2009/0155378 A1 | 6/2009 | Behnam et al. |
| 2009/0319045 A1 | 12/2009 | Truncale et al. |
| 2010/0042216 A1 | 2/2010 | Kilpela et al. |
| 2010/0286783 A1 | 11/2010 | Lechmann et al. |
| 2011/0144766 A1 | 6/2011 | Kale et al. |

* cited by examiner

INTERBODY BONE IMPLANT DEVICE

This application claims the benefit of and is a continuation application of U.S. patent application Ser. No. 13/448,647 filed on Apr. 17, 2012, entitled "INTERBODY BONE IMPLANT DEVICE". This entire disclosure is incorporated herein by reference into the present disclosure.

BACKGROUND

The use of bone grafts and bone substitute materials in orthopedic medicine is known. Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible. The natural cellular healing and remodeling mechanisms of the body coordinate removal of bone and bone grafts by osteoclast cells and formation of bone by osteoblast cells.

In the spinal surgery field, surgical procedures are often performed to correct problems with displaced, damaged or degenerated intervertebral discs due to trauma, disease or aging. Bone graft materials are often used in spine fusion surgery. Current spinal fusion implants utilize grafts of either bone or artificial implants to fill the intervertebral disc space.

In particular, one method of treating a damaged disc is by immobilizing the area around the injured portion and fusing the immobilized portion by promoting bone growth between the immobilized spine portions. This often requires implantation of an intervertebral device to provide the desired spacing between adjacent vertebrae to maintain foraminal height and decompression. That is, an intervertebral implant comprising an interbody fusion device may be inserted into the intervertebral disc space of two neighboring vertebral bodies or into the space created by removal of damaged portions of the spine.

In some instances, a formed implant, whether monolithic or particulated and in a carrier, is substantially solid at the time of implantation and thus does not conform to the implant site. Further, most implants are substantially formed at the time of implantation in limited sizes and shapes and provide little ability for customization.

While generally effective, the use of bone grafts has some limitations. Autologous bone grafts, being obtained from the patient, require additional surgery and present increased risks associated with its harvesting, such as risk of infection, blood loss and compromised structural integrity at the donor site. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, such materials are not as well suited for wrapping or resurfacing bone. Indeed, the use of bone grafts is generally limited by the available shapes and sizes of grafts provided.

With regards to bone grafts, allograft bone is a reasonable bone graft substitute for autologous bone. It is readily available from cadavers and avoids the surgical complications and patient morbidity associated with harvesting autologous bone. Allograft bone is essentially a load-bearing matrix comprising cross-linked collagen, hydroxyapatite, and osteoinductive bone morphogenetic proteins. Human allograft tissue is widely used in orthopaedic surgery.

Indeed, allograft is a preferred material by surgeons for conducting interbody fusions because it will remodel over time into host bone within the fusion mass. However, though allograft tissue has certain advantages over the other treatments, allograft is typically available in only limited size ranges, thus making it difficult to provide implants, in particular, interbody implants in a preferred geometrical shape. Indeed, allograft may only provide temporary support, as it is difficult to manufacture the allograft with a consistent shape and strength.

Accordingly, it would be desirable to construct an implant, particularly an interbody implant, to better utilize the benefits of allograft treatment.

SUMMARY

The present disclosure fills the foregoing need by providing devices (e.g., medical devices), systems and methods for enhancing the utility of allograft tissue as an interbody fusion material. In particular, the present disclosure provides an advantageous implant device comprising a composite of allograft bone tissue and a non-bone composition such as a polymer composition, e.g., poly-ether-ether-ketone (PEEK) and/or other polymer compositions. According to some embodiments, a composite bone implant device is provided which utilizes and retains allograft pieces within a polymer structure. This advantageously enables the beneficial properties of allograft tissue and the beneficial attributes of polymers to be fully realized. For example, the remodeling capability of allograft tissue is advantageously combined with the polymer's ability to enable implants to be formed into any geometrical shape or size.

According to one aspect, a bone implant device is provided comprising a body, which comprises a non-bone composition formed into a shape and including at least one cavity; and a biocompatible material provided within said at least one cavity of the body, wherein the body is formable into a shape and size adapted for implantation at a surgical site.

According to another aspect, a composite interbody bone implant device is provided comprising a body, which comprises a non-bone composition formed into a shape and including a plurality of cavities and an osteoinductive material provided within said cavities of the body, wherein the body is formable into a shape and size adapted for implantation at a surgical site.

According to yet another aspect, a composite interbody bone implant device is provided comprising a body comprises a polymer formed into a shape and including a plurality of cavities, and an allograft material provided within said cavities of the body, wherein the body is formable into a shape and size adapted for implantation at a surgical site.

While multiple embodiments are disclosed, still other embodiments of the present disclosure will become apparent to those skilled in the art from the following detailed description, which is to be read in connection with the accompanying drawing(s). As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

In part, other aspects, features, benefits and advantages of the embodiments will be apparent with regard to the following description, appended claims and accompanying drawing(s) where:

DEFINITIONS

Figure 1:
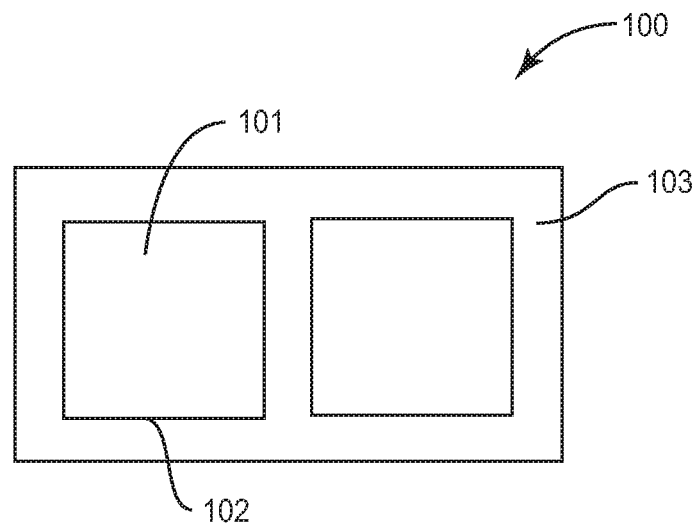
FIG. 1 is a top view of an exemplary composite bone implant device according to one embodiment.

To aid in the understanding of the disclosure, the following non-limiting definitions are provided:

"Bioactive agent or bioactive compound," as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

"Biocompatible," as used herein, refers to materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the disclosure. In some embodiments, demineralized bone has less than 95% of its original mineral content. Demineralized is intended to encompass such expressions as "substantially demineralized," "partially demineralized," and "fully demineralized."

"Demineralized bone matrix" or "DBM" as used herein, refers to any material generated by removing mineral material from bone tissue. In some embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the disclosure.

"Osteoconductive," as used herein, refers to the ability of a non-osteoinductive substance to serve as a suitable template or substance along which bone may grow.

"Osteogenic," as used herein, refers to the ability of an agent, material, or implant to enhance or accelerate the growth of new bone tissue by one or more mechanisms such as osteogenesis, osteoconduction, and/or osteoinduction.

"Osteoimplant," as used herein, refers to any bone-derived implant prepared in accordance with the embodiments of this disclosure and therefore is intended to include expressions such as bone membrane, bone graft, etc.

"Osteoinductive," as used herein, refers to the quality of being able to recruit cells from the host that have the potential to stimulate new bone formation. Any material that can induce the formation of ectopic bone in the soft tissue of an animal is considered osteoinductive.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "morbidity" refers to the frequency of the appearance of complications following a surgical procedure or other treatment.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, a collagen matrix seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols, which have only a marginal effect on the patient.

The term "xenograft" refers to tissue or organs from an individual of one species transplanted into or grafted onto an organism of another species, genus, or family.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Certain terminology, which may be used in the following description is for convenience only and is not limiting. For example, the words "right", "left", "top" and "bottom" designate directions in the drawings to which reference is made. The words, "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

Bone allograft is a preferred material by surgeons for conducting interbody fusions because it will remodel over time into host bone within the fusion mass, but a limitation with the allograft is that it is only available in limited size ranges making it difficult to provide interbody implants in a preferred geometrical shape. On the other hand, synthetic polymers such as poly-ether-ether-ketone (PEEK) can be manufactured into any geometrical shape, but have some strength limitations and are a permanent implant that will not remodel into host bone over time like an allograft. Polymer compositions also do not allow for direct bone attachment or bonding to further stabilize the implant and fusion mass.

The present disclosure overcomes the drawbacks by providing various exemplary designs of bone implants comprising a composite of allograft tissue and a non-bone material, such as a polymer (or other materials such as metal, ceramic or plastic). One exemplary configuration according to the present disclosure involves providing cortical allograft pieces that are mechanically interlocked together to form a single interbody implant. A body, which comprises a non-bone material is provided having cavities or inserts formed therein which are configured to retain the allograft pieces. This composite design of the body and an allograft allows for the advantageous properties of each to be fully realized. According to one aspect, the body may be configured to retain as many allograft pieces as possible in order to optimize the surface area contact of the allograft with intervertebral endplates.

In some embodiments, the composite implant is configured to increase the surface area contact of the allograft with the host bone, which will result in faster fusion and incorporation of the composite implant into host bone and ultimately a stronger fusion mass. In some embodiments, the allograft bone used in the implant is surface demineralization to increase its osteoinductivity and fusion with the host bone. In some embodiments, the implant optimizes the non-bone and bone content of the implant body such that the majority of the mechanical load is carried by the allograft and the non-bone material's primary purpose is to hold the allograft pieces together.

In some embodiments, the portion of the allograft that is not demineralized comprises load bearing and/or higher compressive strength allograft material. Advantageously, it is noted that an implant device may be provided in any configuration, size and shape, as per the requirements of the desired target site. Thus, an almost unlimited ranges of sizes and shapes of optimized bone implant devices may be provided. In one example, an implant device may be configured to be adapted for use as an interbody fusion device, e.g., in spinal fusion procedures. However, alternate configurations of the implant device may be contemplated to suit the needs of a patient's bone graft target site.

Radiographically, a fusion enabled with an implant device according to the present disclosure will be easier to assess because of masking by the solid material of the non-bone material. Such a composite design also allows for more advanced insertion tools and interbody cage features such as a cage inserter that rotates the implant towards the center of the disc as it is inserted. Such as feature is very difficult to incorporate into a pure allograft implant.

Another advantage is that an implant body according to the present disclosure can be inserted on its side and once in the disc space rotated 90 degrees to jack open or distract open the disc space.

Figure 2:
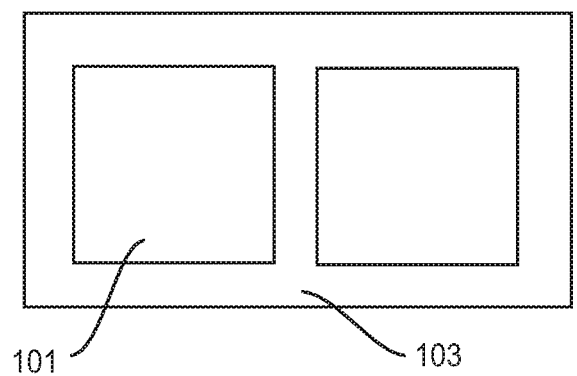
FIG. 2 is a front view of the device of FIG. 1.

FIG. 1 is a top view of an exemplary composite bone implant device 100 according to one embodiment. FIG. 2 is a front view of the device of FIG. 1. Device 100 may be comprises a body 103 which may comprise, e.g., a 'skeleton' structure configured to include at least one window or cavity 102, within which a substance 101, such as an allograft material may be inserted and retained. The term 'cavity' includes and encompasses voids, apertures, bores, depressions, holes, indentations, grooves, channels, notches or the like. In some embodiments as shown, a plurality of cavities 102 may be provided throughout one or more surfaces of and/or within the body 103, thus enabling a plurality of allograft pieces to be retained by the body 103 in various locations.

The body 103 may comprise any non-bone composition, in particular, any biocompatible material including but not limited to a metal, such as, for example, cobalt-chromium-molybdenum (CCM) alloys, titanium, titanium alloys, stainless steel, aluminum, etc., a ceramic such as, for example, zirconium oxide, silicone nitride, etc., an allograft, an autograft, a metal-allograft composite, a polymer such as, for example, polyaryl ether ketone (PAEK), polyether ether ketone (PEEK), polyether ketone ketone (PEKK), polyetherketone (PEK), polyetherketone ether-ketone-ketone (PEKEKK), etc. The polymers may be reinforced with a fiber such as, for example, a carbon fiber or other thin, stiff fiber.

Advantageously, the body 103 may be formed, e.g., via injection molding and/or machining into any size or shape to accommodate the desired application and/or delivery conditions. The body 103 may further be configured to include any desired features, such as cavities, projections, etc. in any desired location or orientation, as discussed further below.

Figure 10:
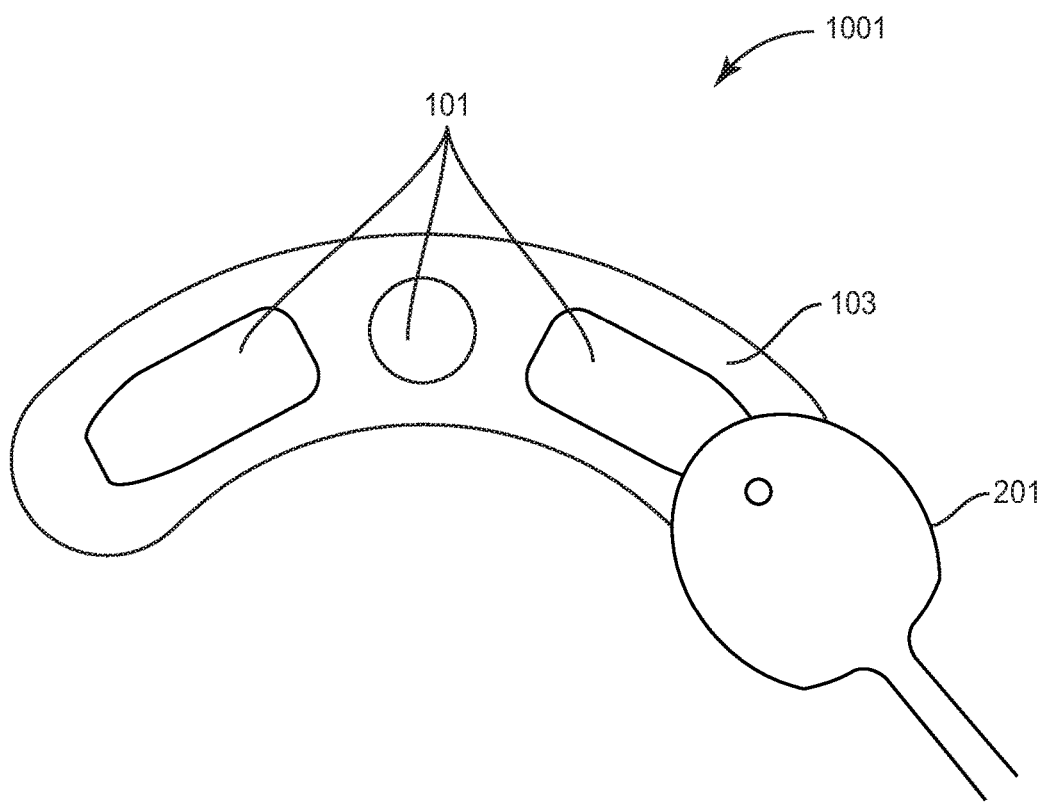
FIG. 10 is an exemplary depiction of an implant device secured by an insertion tool.

The body 103 may also include a mechanism or feature for engaging an implant insertion instrument (shown in FIG. 10). The mechanism or feature for engaging the insertion instrument may take on any form including, for example, one or more bores for receiving one or more projections (not shown) formed on the implant insertion instrument, one or more projections (not shown) for engaging one or more bores (not shown) formed on the implant insertion instrument, one or more channels (not shown) for receiving one or more tips formed on the implant insertion instrument, one or more threaded bores (not shown) for receiving one or more threaded shafts or screws, etc.

The body 103 may also include a mechanism or features for reducing and/or preventing slippage or migration of the implant device 100 during insertion. For example, one or more surfaces of the body 103 may include projections such as ridges or teeth (not shown) for increasing the friction between the device 100 and the adjacent contacting surfaces of the vertebral bodies so to prevent movement of the implant device 100 after introduction to a desired disc space.

In some embodiments, the surfaces of the body 103 include at least one cavity 102 or a plurality of cavities 102. Each cavity 102 may be provided in any of a variety of shapes in addition to the generally rectangular shape shown, e.g., in FIGS. 1 and 2, including but not limited to generally circular, oblong, curved, triangular and other polygonal or non-polygonal shapes. The same or different types of cavity shapes and sizes may be provided in each body 103. Each cavity 102 may be formed to pass entirely through the body 103 for promoting fusion between the upper and lower vertebral bodies so as to allow a boney bridge to form through the implant device 100. Alternately, cavities 102 may be formed to partially pass through the body 103, or may be formed only on one or more surfaces thereof.

In addition to the body 103 being enabled to be provided in various configurations, shapes and sizes, the body 103 may include any number of cavities 102 in different arrangements, locations, sizes and shapes. For example, the arrangement and location of cavities 102 may be determined based on application of the implant device 100. Alternate embodiments showing non-limiting examples of the various arrangements of cavities 102 are shown in FIGS. 3-9 and discussed further below.

According to some embodiments, fusion may be facilitated or augmented by introducing or positioning various osteoinductive materials within the cavities in the implant device. Such osteoinductive materials may be introduced before, during, or after insertion of the exemplary implant device, and may include (but are not necessarily limited to) autologous bone harvested from the patient receiving the implant device, bone allograft, bone xenograft, any number of non-bone implants (e.g. ceramic, metallic, polymer), bone morphogenic protein, and/or bio-resorbable compositions.

Figure 3:
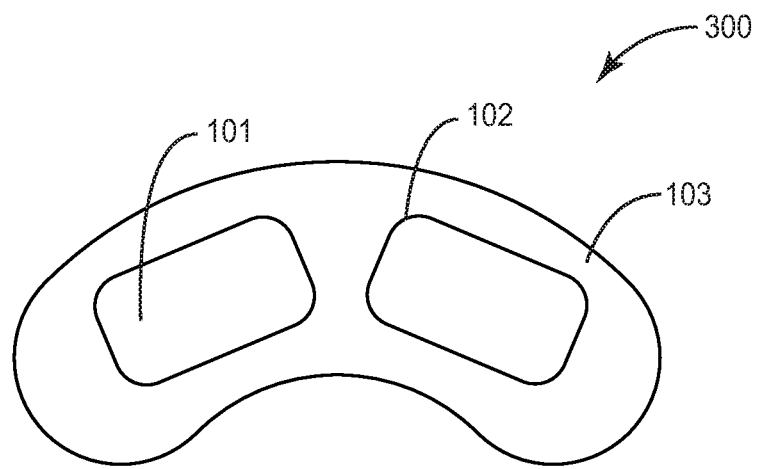
FIGS. 3-4 are top views of exemplary composite interbody bone implant devices for transforaminal lumbar interbody fusion (TLIF) according to alternate embodiments.
Figure 4:
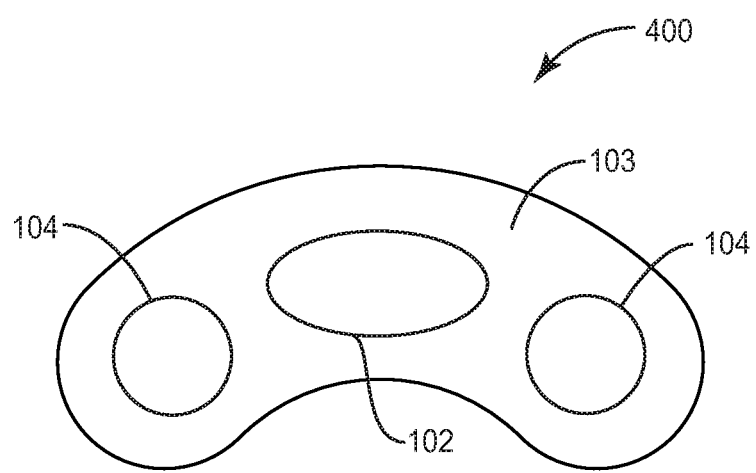

FIGS. 3-4 are top views of exemplary composite interbody bone implant devices 300, 400 for transforaminal lumbar interbody fusion (TLIF) according to alternate embodiments. Devices for TLIF procedures may be formed in a generally crescent shape, as shown, to be best adapted to the surgical site. Exemplary device 300 depicts two rectangular cavities 102 in which a substance 101, such as an osteoinductive material, may be retained, while exemplary device 400 depicts a center oval cavity 102 and two adjacent circular cavities 104 in which a substance 101, such as an osteoinductive material, may be retained.

Figure 5:
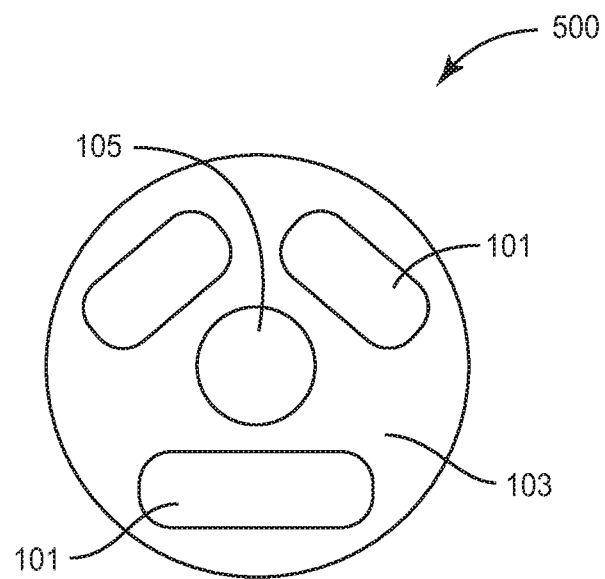
FIGS. 5, 7 and 8 are top views of exemplary composite interbody bone implant devices for anterior lumbar interbody fusion (ALIF) according to alternate embodiments.
Figure 6:
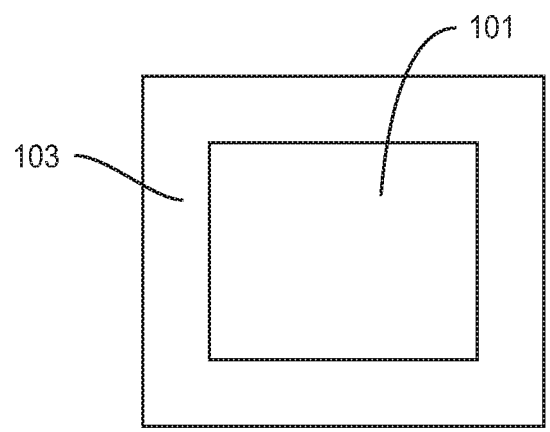
FIG. 6 is a side view of the device of FIG. 5.
Figure 7:
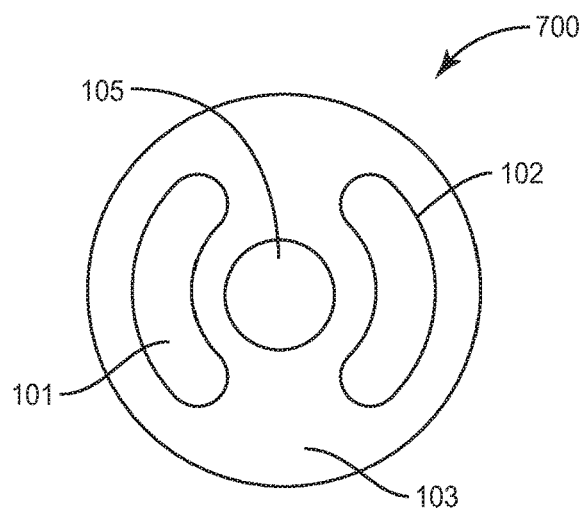
Figure 8:
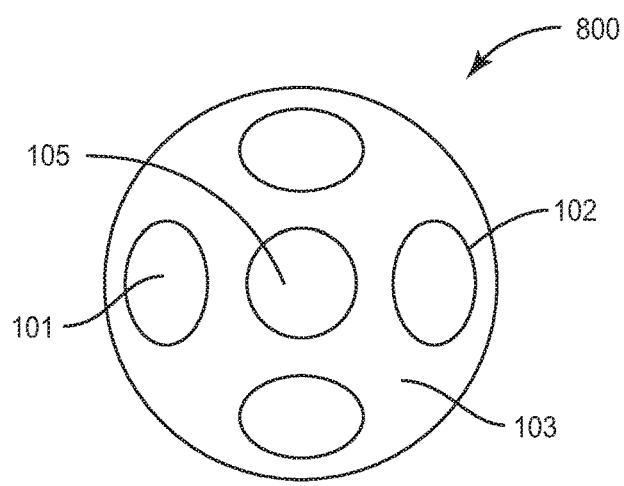

FIGS. 5, 7 and 8 are top views of exemplary composite interbody bone implant devices for anterior lumbar interbody fusion (ALIF) according to alternate embodiments. FIG. 6 is a side view of the device of FIG. 5. Devices for ALIF procedures may be formed in a generally circular shape, preferably with a hole 105 formed in substantially a center thereof. Exemplary device 500 depicts three rectangular cavities arranged around a hole 105. A substance 101, such as an osteoinductive material, may be retained in the cavities. Exemplary device 700 depicts two curved crescent-shaped cavities arranged around a hole 105. A substance 101, such as an osteoinductive material, may be retained in the cavities 102. Exemplary device 800 depicts four oval cavities 102 arranged around a hole 105, wherein a substance such as an osteoinductive material 101 may be retained within the cavities 102. The body 103 of the device is shown in FIGS. 1-12.

In some embodiments, the implant device contacts host bone and the implant device comprises non-bone material, the contact surface area of the non-bone material and the cortical bone to the host bone comprises from about 5% to about 50% or from about 10% to about 20% of the implant.

In some embodiments, the implant device comprises non-bone material and the non-bone material comprises from about 10 wt. % to about 60 wt. % of the implant. In some embodiments, the implant device comprises bone material and the bone material comprises from about 10 wt. % to about 60 wt. % of the implant.

In some embodiments, the bone allograft material comprises demineralized bone matrix fibers and demineralized bone matrix chips in a ratio of 25:75 to about 75:25 fibers to chips.

In some embodiments, the device comprises a plurality of cavities where all or some of the plurality of cavities are empty and configured to receive bone graft material, autograft bone material, ceramic bone void fillers, demineralized bone matrix, or one or more growth factors. The cavities can be partially or completely filled before the device is implanted. The filling can occur in, for example, the operating room before the device is implanted into the subject.

In some embodiments, the composite interbody bone implant may comprise an allograft portion that is configured to be joined to another allograft portion or a non-allograft portion comprising a polymer. In this way, the composite interbody device can be joined before it is implanted at or neat the target site. The composite interbody implant can have mating surfaces comprising recesses and/or projections and reciprocating recesses and/or projections (e.g., joints) that allow the implant to be assembled before implantation. Assembly can also include, for example, use of an adhesive material to join parts of the implant together and provide strong interlocking fit.

The adhesive material may comprise polymers having hydroxyl, carboxyl, and/or amine groups. In some embodiments, polymers having hydroxyl groups include synthetic polysaccharides, such as for example, cellulose derivatives, such as cellulose ethers (e.g., hydroxypropylcellulose). In some embodiments, the synthetic polymers having a carboxyl group, may comprise poly(acrylic acid), poly(methacrylic acid), poly(vinyl pyrrolidone acrylic acid-N-hydroxysuccinimide), and poly(vinyl pyrrolidone-acrylic acid-acrylic acid-N-hydroxysuccinimide) terpolymer. For example, poly(acrylic acid) with a molecular weight greater than 250,000 or 500,000 may exhibit particularly good adhesive performance. In some embodiments, the adhesive can be a polymer having a molecular weight of about 2,000 to about 5,000, or about 10,000 to about 20,000 or about 30,000 to about 40,000.

In some embodiments, the adhesive can comprise imido ester, p-nitrophenyl carbonate, N-hydroxysuccinimide ester, epoxide, isocyanate, acrylate, vinyl sulfone, orthopyridyl-disulfide, maleimide, aldehyde, iodoacetamide or a combination thereof. In some embodiments, the adhesive material can comprise at least one of fibrin, a cyanoacrylate (e.g., N-butyl-2-cyanoacrylate, 2-octyl-cyanoacrylate, etc.), a collagen-based component, a glutaraldehyde glue, a hydrogel, gelatin, an albumin solder, and/or a chitosan adhesives. In some embodiments, the hydrogel comprises acetoacetate esters crosslinked with amino groups or polyethers as mentioned in U.S. Pat. No. 4,708,821. In some embodiments, the adhesive material can comprise poly(hydroxylic) compounds derivatized with acetoacetate groups and/or polyamino compounds derivatized with acetoacetamide groups by themselves or the combination of these compounds crosslinked with an amino-functional crosslinking compounds.

The adhesive can be a solvent based adhesive, a polymer dispersion adhesive, a contact adhesive, a pressure sensitive adhesive, a reactive adhesive, such as for example multi-part adhesives, one part adhesives, heat curing adhesives, moisture curing adhesives, or a combination thereof or the like. The adhesive can be natural or synthetic or a combination thereof.

Contact adhesives are used in strong bonds with high shear-resistance. Pressure sensitive adhesives form a bond by the application of light pressure to bind the adhesive with the target tissue site, cannula and/or expandable member. In some embodiments, to have the device adhere to the target tissue site, pressure is applied in a direction substantially perpendicular to a surgical incision.

Multi-component adhesives harden by mixing two or more components, which chemically react. This reaction causes polymers to cross-link into acrylics, urethanes, and/or epoxies. There are several commercial combinations of multi-component adhesives in use in industry. Some of these combinations are: polyester resin-polyurethane resin; polyols-polyurethane resin, acrylic polymers-polyurethane resins or the like. The multi-component resins can be either solvent-based or solvent-less. In some embodiments, the solvents present in the adhesives are a medium for the polyester or the polyurethane resin. Then the solvent is dried during the curing process.

In some embodiments, the adhesive can be a one-part adhesive. One-part adhesives harden via a chemical reaction with an external energy source, such as radiation, heat, and moisture. Ultraviolet (UV) light curing adhesives, also known as light curing materials (LCM), have become popular within the manufacturing sector due to their rapid curing time and strong bond strength. Light curing adhesives are generally acrylic based. The adhesive can be a heat-curing adhesive, where when heat is applied (e.g., body heat), the components react and cross-link. This type of adhesive includes epoxies, urethanes, and/or polyimides. The adhesive can be a moisture curing adhesive that cures when it reacts with moisture present (e.g., bodily fluid) on the substrate surface or in the air. This type of adhesive includes cyanoacrylates or urethanes. The adhesive can have natural components, such as for example, vegetable matter, starch (dextrin), natural resins or from animals e.g. casein or animal glue. The adhesive can have synthetic components based on elastomers, thermoplastics, emulsions, and/or thermosets including epoxy, polyurethane, cyanoacrylate, or acrylic polymers.

In some embodiments, the interbody bone implant may be joined together utilizing pins, rods, clips, or other fasteners to allow strong and easily coupling of component parts. In some embodiments, the allograft material is configured to provide the most contact to tissue surfaces (e.g., the allograft material can be on the perimeter of the device, while the polymer material is situated in the interior of the device.

Figure 9:
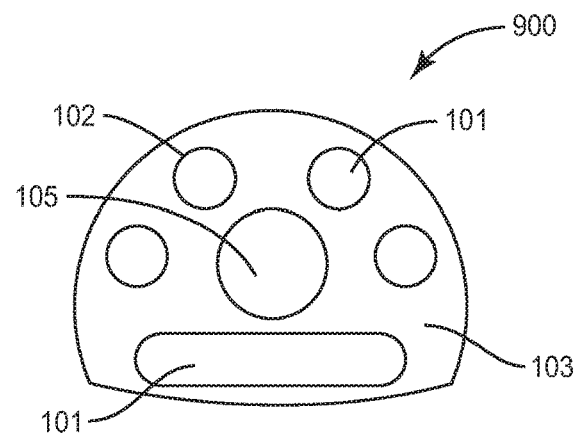
FIG. 9 is a top view of an exemplary composite interbody bone implant device for anterior cervical discectomy and fusion (ACDF) according to an alternate embodiment.

FIG. 9 is a top view of an exemplary composite interbody bone implant device for anterior cervical discectomy and fusion (ACDF) according to an alternate embodiment. Devices for ACDF procedures may be formed in a general D-shape, preferably with a hole 105 formed substantially in a center thereof. Exemplary device 900 depicts four circular cavities 102 arranged around a hole 105, and a rectangular cavity opposed to the four holes. A substance such as a biocompatible material may be inserted and retained within the cavities 102. The biocompatible material may comprise, e.g., an osteoinductive material 101.

In one embodiment, the osteoinductive material comprises allograft tissue. Non-limiting examples of a bone graft material include demineralized bone matrix, or a bone composite. While allograft bone is a desirable alternative to autograft, it must be rigorously processed and terminally sterilized prior to implantation to remove the risk of disease transmission or an immunological response. This processing removes the osteogenic and osteoinductive properties of the allograft, leaving only an osteoconductive scaffold. These scaffolds are available in a range of preparations (such as morselized particles and struts) for different orthopedic applications.

In one embodiment, to improve the osteoinductive properties, it is desirable to use demineralized bone matrix (DBM) as the osteoinductive material, due to its superior biological properties relative to undemineralised allograft bone, since the removal of minerals increases the osteoinductivity of the graft. Currently, there are a range of DBM products in clinical use.

Demineralized bone matrix (DBM) is demineralized allograft bone with osteoinductive activity. DBM is prepared by acid extraction of allograft bone, resulting in loss of most of the mineralized component but retention of collagen and noncollagenous proteins, including growth factors. DBM does not contain osteoprogenitor cells, but the efficacy of a demineralized bone matrix as a bone-graft substitute or extender may be influenced by a number of factors, including the sterilization process, the carrier, the total amount of bone morphogenetic protein (BMP) present, and the ratios of the different BMPs present. DBM includes demineralized pieces of cortical bone to expose the osteoinductive proteins contained in the matrix. These activated demineralized bone particles are usually added to a substrate or carrier (e.g. glycerol or a polymer). DBM is mostly an osteoinductive product, but lacks enough induction to be used on its own in challenging healing environments such as posterolateral spine fusion.

According to some embodiments of the disclosure, the demineralized bone matrix may comprise demineralized bone matrix fibers and/or demineralized bone matrix chips. In some embodiments, the demineralized bone matrix may comprise demineralized bone matrix fibers and demineralized bone matrix chips in a 30:60 ratio.

According to one embodiment of the disclosure, the bone composite comprises a bone powder, a polymer and a demineralized bone. In different embodiments of the disclosure, bone powder content can range from about 5% to about 90% w/w, polymer content can range from about 5% to about 90% w/w, and demineralized bone particles content comprises the reminder of the composition. Preferably, the demineralized bone particles comprise from about 20% to about 40% w/w while the polymer and the bone powder comprise each from about 20% to about 60% w/w of the composition. The bone graft materials of the present disclosure include those structures that have been modified in such a way that the original chemical forces naturally present have been altered to attract and bind molecules, including, without limitation, growth factors and/or cells, including cultured cells.

Namely, the demineralized allograft bone material may be further modified such that the original chemical forces naturally present have been altered to attract and bind growth factors, other proteins and cells affecting osteogenesis, osteoconduction and osteoinduction. For example, a demineralized allograft bone material may be modified to provide an ionic gradient to produce a modified demineralized allograft bone material, such that implanting the modified demineralized allograft bone material results in enhanced ingrowth of host bone.

In one embodiment an ionic force change agent may be applied to modify the demineralized allograft bone material. The demineralized allograft bone material may comprise, e.g., a demineralized bone matrix (DBM) comprising fibers, particles and any combination of thereof. According to another embodiment, a bone graft structure may be used which comprises a composite bone, which includes a bone powder, a polymer and a demineralized bone.

The ionic force change agent may be applied to the entire demineralized allograft bone material or to selected portions/surfaces thereof.

The ionic force change agent may be a binding agent, which modifies the demineralized allograft bone material or bone graft structure to bind molecules, such as, for example, growth factors, or cells, such as, for example, cultured cells, or a combination of molecules and cells. In the practice of the disclosure the growth factors include but are not limited to BMP-2, rhBMP-2, BMP-4, rhBMP-4, BMP-6, rhBMP-6, BMP-7(OP-1), rhBMP-7, GDF-5, LIM mineralization protein, platelet derived growth factor (PDGF), transforming growth factor-β (TGF-β), insulin-related growth factor-I (IGF-I), insulin-related growth factor-II (IGF-II), fibroblast growth factor (FGF), beta-2-microglobulin (BDGF II), and rhGDF-5. A person of ordinary skill in the art will appreciate that the disclosure is not limited to growth factors only. Other molecules can also be employed in the disclosure. For example, tartrate-resistant acid phosphatase, which is not a growth factor, may also be used in the disclosure.

If a cell culture is employed, the cells include but are not limited to mesenchymal stems cells, pluripotent stem cells, osteoprogenitor cells, osteoblasts, osteoclasts, and any bone marrow-derived cell lines.

In some embodiments, the ionic force change agent comprises at least one of enzymes, enzyme mixtures, pressure (e.g., isostatic pressure), chemicals, heat, sheer force, oxygen plasma, or a combination thereof. For example, the ionic force change agent may comprise an enzyme such as collagenase or pepsin, which can be administered for a sufficient period of time to partially digest at least a portion of the demineralized allograft bone material. Subsequently, the enzyme may be deactivated and/or removed.

Any enzyme or enzyme mixture may be contemplated, and treatment time durations may be altered in accordance with the enzyme(s) used. Some suitable enzymes that may degrade the DBM material include, but are not limited to, cysteine proteinases, matrix metalloproteinases, enzymes such as amylases, proteases, lipases, pectinases, cellulases, hemicellulases, pentosanases, xylanases, phytases or combinations thereof. Exemplary enzymes suitable to partially degrade and modify the DBM material, include but are not limited to, cathepsin L, cathepsin K, cathepsin B, collagenase, pepsin, plasminogen, elastase, stromelysin, plasminogen activators, or a combination thereof.

In some embodiments, the DBM material can be subjected to pressure to modify it. The simplest pressing technique is to apply pressure to the unconstrained DBM material. Examples include pressing the DBM material using a mortar and pestle, applying a rolling/pressing motion such as is generated by a rolling pin, or pressing the bone pieces between flat or curved plates. These flattening pressures cause the DBM material fibers to remain intact.

Another pressing technique involves mechanically pressing demineralized bone material, which can be constrained within a sealed chamber having a hole (or a small number of holes) in its floor or bottom plate. The separated fibers extrude through the holes with the hole diameter limiting the maximum diameter of the extruded fibers. This constrained technique results in fibers that are largely intact (as far as length is concerned).

In a combined unconstrained/constrained pressing technique that results in longer fibers by minimizing fiber breakage, the demineralized bone is first pressed into an initially separated mass of fibers while in the unconstrained condition and thereafter these fibers are constrained within the sealed chamber where pressing is continued.

In general, pressing of demineralized bone to provide demineralized bone particles can be carried out at from about 1,000 to about 40,000 psi, and preferably at from about 5,000 to about 20,000 psi.

Subsequent to the addition of the ionic force change agent, the practitioner may optionally administer an appropriate molecule or cell culture. Generally, the molecule or cell culture is applied within minutes, for example from about 1 to about 120 minutes before implantation into the patient.

One class of molecules suitable for one embodiment of the disclosure is growth factors. Growth factors suitable for use in the practice of the disclosure include but are not limited to bone morphogenic proteins, for example, BMP-2, rhBMP-2, BMP-4, rhBMP-4, BMP-6, rhBMP-6, BMP-7 (OP-1), rhBMP-7, GDF-5, and rhGDF-5. Bone morphogenic proteins have been shown to be excellent at growing bone and there are several products being tested. For example, rhBMP-2 delivered on an absorbable collagen sponge (INFUSE® Bone Graft, Medtronic Sofamor Danek, Memphis, Tenn.) has been used inside titanium fusion cages and resulted in successful fusion and can be used on a ceramic carrier to enhance bone growth in a posterolateral fusion procedure. rhBMP-2 can also be used on a carrier for acute, open fractures of the tibial shaft. BMP-7 (OP-1) also enhances bone growth in a posterolateral fusion procedure.

Additionally, suitable growth factors include, without limitation, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), and beta-2-microglobulin (BDGF II).

Further, molecules, which do not have growth factor properties may also be suitable for this disclosure. An example of such molecules is tartrate-resistant acid phosphatase.

In one embodiment, the demineralized allograft bone material is treated with a negatively-charged ionic force change agent to produce a negatively-charged demineralized allograft bone material. The negatively-charged demineralized allograft bone material attracts a positively charged molecule having a pI from about 8 to about 10. Examples of positively charged molecules having a pI from about 8 to about 10 include but are not limited to, rhBMP-2 and rhBMP-6.

In another embodiment, the demineralized allograft bone material is treated with a positively-charged ionic force change agent such that the positively-charged demineralized allograft bone material attracts a molecule with a slightly negative charge, for example a charge of pI about 5 to about 7. Examples of molecules having a slightly negative charge include rhBMP-4.

In yet another embodiment, the demineralized allograft bone material is treated with a positively-charged ionic force change agent to produce a positively-charged demineralized allograft bone material such that cells, in particular cell cultures having a negative surface charge bind to the positively-charged demineralized allograft bone material. Examples of cells which are suitable for use in the practice of the disclosure include but are not limited to mesenchymal stems cells, pluripotent stem cells, embryonic stem cells, osteoprogenitor cells and osteoblasts.

The mechanisms by which a demineralized allograft bone material may acquire ionic forces include but are not limited to ionization, ion adsorption and ion dissolution.

In one embodiment, the implant is modified to give it the selected charge by a one-to-one substitution of the calcium ion with lithium, sodium, potassium or cesium of hydroxyapatite.

In yet another aspect, treatments with gradient-affecting elements, such as elements present in hydroxyapatite, and human proteins are employed. Suitable gradient-affecting proteins are those present in the organic phase of human bone tissue. The gradient-affecting proteins derive molecule or cell attraction without the potential damaging effects on the implants, as may be the case with other chemical treatments. Usually this is accomplished through surface treatments such as, for example, plasma treatment to apply an electrostatic charge on bone.

The term "plasma" in this context is an ionized gas containing excited species such as ions, radicals, electrons and photons. The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces. Plasma treatment is an effective method to uniformly alter the surface properties of substrates having different or unique size, shape and geometry including but not limited to bone and bone composite materials.

In some embodiments, the implant device 100 of the present disclosure having osteoinductive material retained therein may be used to provide temporary or permanent fixation along an orthopedic target site. For example, the implant device 100 may be introduced into an intervertebral disc space while secured to a surgical insertion instrument and thereafter manipulated into the proper orientation before being released. According to one aspect, the implant device 100 may be introduced into a target site through use of any of a variety of suitable surgical instruments having the capability to engage the implant device 100. For example, a clinician may utilize the implant 100 in a minimally invasive spinal fusion procedure. After creation of a working channel and preparation of the disc space, a single implant device 100 may be grasped and placed into the intervertebral disc space. Additional materials and tools may be included in the procedure before, during, or after the insertion of the implant 10 to aid in introducing the implant into a targeted spinal site.

FIG. 10 is an exemplary depiction of an implant device 1001 grasped by an insertion tool 201. The tool 201 may be adapted to be affixed to the particular dimensions of the implant device 1001 for secure and effective manipulation of the device during implantation procedures. Advantageously, the tool 201 may enable rotation of the implant device 1001 within an intervertebral space after insertion therein. The device can have a substance disposed in any one of the cavities.

Figure 11:
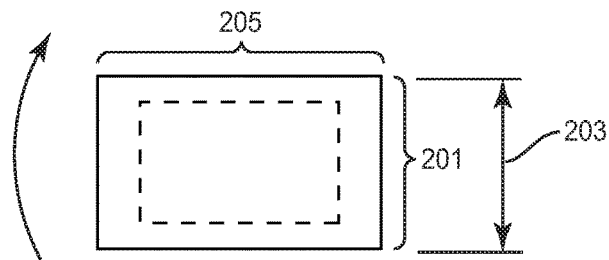
FIG. 11 depicts side and top views of an exemplary implant device inserted within an intervertebral disc space in a first position.
Figure 11:
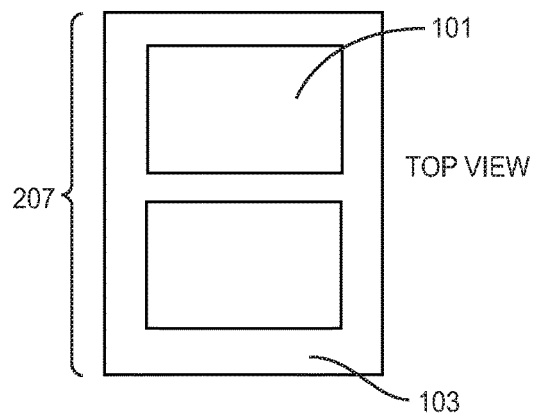
Figure 12:
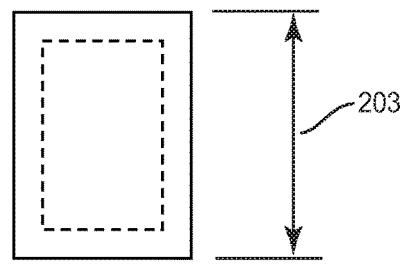
FIG. 12 depicts side and top views of an exemplary implant device inserted within an intervertebral disc space and rotated to a second position.
Figure 12:
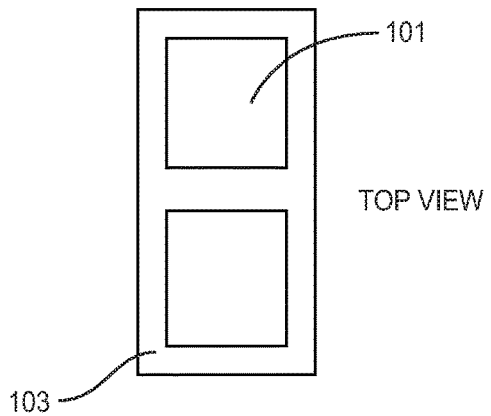

FIG. 11 depicts side and top views of an exemplary implant device inserted within an intervertebral disc space 203 in a first position. FIG. 12 depicts side and top views of an exemplary implant device inserted within an intervertebral disc space 203 and rotated to a second position, which causes the disc space 203 to be increased.

To facilitate rotation and effective distraction, an implant device according to the present disclosure may be formed having a shape and dimensions to provide, e.g., a desired amount of self-distraction of the disc space during insertion of the implant device. For example, in some embodiments as shown in FIGS. 11 and 12, an implant device is provided which is formed to have a thickness 201 which is less than at least one of its length 207 and width 205. Initially, the implant device may be inserted to have its thickness 201 placed within the disc space 203. The implant device, being advantageously configured to be effectively grasped by a surgical instrument, may then be rotated (e.g., 90 degrees in either direction) to effectively jack open or distract open the disc space by causing the increased dimensions of either the length or width to be placed between the disc space 203. The device can have a substance 101 disposed in the cavity of uniformly throughout the body 103 or at discrete positions in the cavity or body 103.

Having been deposited in the disc space, an implant device of the present disclosure effects spinal fusion over time as the natural healing process integrates and binds the implant within the intervertebral space by allowing a boney bridge to form through the implant and between the adjacent vertebral bodies.

In some embodiments, an implant device of the present disclosure may be used to deliver substances such as surface demineralized bone chips, optionally of a predetermined particle size, demineralized bone fibers, optionally pressed, and/or allograft.

For embodiments where the substance is biologic, the substance may be autogenic, allogenic, xenogenic, or transgenic. However, it is contemplated that other suitable materials may be positioned in the implant device such as, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In some embodiments, the substance may be pressed before placement in the implant device. A substance provided within the implant device may be homogenous, or generally a single substance, or may be heterogeneous, or a mixture of substances.

In some embodiments, the substance may be designed to expand in vivo. Such an embodiment may be used to fill a space and create contact with congruent surfaces as it expands in vivo, for example for interbody fusion. Thus, in some embodiments, the implant device may be used in the disc space, between implants, or inside a cage.

In some embodiments the substance delivered by the implant device may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, e.g., SEMA3, controls vascular morphogenesis by inhibiting integrin function in the vascular system, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-β); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In one embodiment of an implant device comprising at least one cavity, it may be contemplated that any combination or mixture of same or different substances may be placed and retained therein, and further, different substances may be placed within the same or different cavities.

Sterilization

A medical implant device according to the present disclosure including its contents may be sterilizable. In various embodiments, one or more components of the implant device and/or its contents are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the medical device has gel components.

Other methods may also be used to sterilize the device and/or one or more components of the device and/or contents, including, but not limited to, gas sterilization, such as, for example, with ethylene oxide or steam sterilization.

Method of Use

An implant device according to the present disclosure delivers the substance or substances in vivo. Active delivery of the substance may include the cleavage of physical and/or chemical interactions of substance from covering with the presence of body fluids, extracellular matrix molecules, enzymes or cells. Further, it may comprise formation change of substances (growth factors, proteins, polypeptides) by body fluids, extracellular matrix molecules, enzymes or cells.

The body of the implant device is loaded with the substance for placement in vivo. The body may be pre-loaded, thus loaded at manufacture, or may be loaded in the operating room or at the surgical site. Preloading may be done with any of the substances previously discussed including, for example, allograft such as DBM, synthetic calcium phosphates, synthetic calcium sulfates, enhanced DBM, collagen, carrier for stem cells, and expanded cells (stem cells or transgenic cells). Loading in the operating room or at the surgical site may be done with any of these materials and further with autograft and/or bone marrow aspirate.

Any suitable method may be used for loading a substance in the implant device in the operating room or at the surgical site. For example, the substance may be spooned into the cavity(ies) of the implant device, the substance may be placed in the implant device using forceps, the substance may be loaded into the implant device using a syringe (with or without a needle), or the substance may be inserted into the implant device in any other suitable manner. Specific embodiments for loading at the surgical site include for example, vertebroplasty or interbody space filler.

For placement, the substance or substances may be provided in the implant device and the implant device placed in vivo. In one embodiment, the implant device is placed in vivo by placing the implant device in a catheter or tubular inserter and delivering the implant device with the catheter or tubular inserter. The implant device, with a substance provided therein, may be steerable such that it can be used with flexible introducer instruments for, for example, minimally invasive spinal procedures. For example, the implant device may be introduced down a tubular retractor or scope, during XLIF, TLIF, or other procedures. In other embodiments, the implant device (with or without substance loaded) may be placed in a cage, for example, for interbody fusion.

Attachment mechanisms provided on the implant device may be used to couple the device to a site in vivo.

Applications

An implant device according to the present disclosure may be configured for use in any suitable application. In some embodiments, the implant device may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The implant device may be used in a minimally invasive procedure via placement through a small incision, via delivery through a tube, or other. The size and shape of the device may advantageously be designed in accordance with restrictions on delivery conditions.

An exemplary application for using an implant device as disclosed is fusion of the spine. In clinical use, the implant device and delivered substance may be used to bridge the gap between the transverse processes of adjacent or sequential vertebral bodies. The implant device may be used to bridge two or more spinal motion segments. The implant device surrounds the substance to be implanted, and contains the substance to provide a focus for healing activity in the body.

In other applications, the implant device may be applied to transverse processes or spinous processes of vertebrae.

Generally, the implant device may be applied to a pre-existing defect, to a created channel, or to a modified defect. Thus, for example, a channel may be formed in a bone, or a pre-existing defect may be cut to form a channel, for receipt of the implant device. The implant device may be configured to match the channel or defect. In some embodiments, the configuration of the implant device may be chosen to match the channel. In other embodiments, the channel may be created, or the defect expanded or altered, to reflect a configuration of the implant device. The implant device may be placed in the defect or channel and, optionally, coupled using attachment mechanisms.

At the time just prior to when the implant device is to be placed in a defect site, optional materials, e.g., autograft bone marrow aspirate, autograft bone, preparations of selected autograft cells, autograft cells containing genes encoding bone promoting action, etc., can be combined with the implant device and/or with a substance provided in the implant device. The implant device can be implanted at the bone repair site, if desired, using any suitable affixation means, e.g., sutures, staples, bioadhesives, screws, pins, rivets, other fasteners and the like or it may be retained in place by the closing of the soft tissues around it.

Although the disclosure has been described with reference to some embodiments, persons skilled in the art will recognize that changes may be made in form and detail without departing from the spirit and scope of the disclosure.

What is claimed is:

1. A composite interbody bone implant device comprising: a body, which comprises a non-bone composition formed into a shape and including a plurality of cavities, the non-bone composition comprising a polymer comprising poly-ether-ketone-ketone (PEKK), poly-ether-ether-ketone (PEEK), or a combination thereof; and an osteoinductive material provided within said cavities of the body, wherein the body is formable into a shape and size configured for implantation at an intervertebral endplate; the osteoinductive material comprising demineralized bone matrix fibers and demineralized bone matrix chips in a 30:60 ratio, and the demineralized bone matrix chips are surface demineralized and the demineralized bone fibers are fully demineralized, wherein the device has a surface area, wherein 5% to 50% of the surface area is configured to contact host bone at the intervertebral endplate and the osteoinductive material further comprises allograft bone material from about 10% to about 60% by weight of the device.

2. A device of claim 1, wherein the allograft bone material is from about 15% to about 30% by weight of the device.

3. A device of claim 2, wherein the polymer comprises poly-ether-ether-ketone (PEEK).

4. A device of claim 1, wherein the non-bone composition includes at least one of an additional polymer, ceramic, metal or combinations thereof.

5. A device of claim 1, wherein the shape of the body is formed by at least one of injection molding and machining.

6. A device of claim 1, wherein some of the plurality of cavities further comprises one or more growth factors.

7. A device of claim 1, wherein the dimensions of the body include a length, a width and a thickness, wherein the thickness of the body is less than at least one of the length and width.

* * * * *

UNITED STATES PATENT AND TRADEMARK OFFICE
CERTIFICATE OF CORRECTION

PATENT NO. : 10,376,381 B2
APPLICATION NO. : 15/643091
DATED : August 13, 2019
INVENTOR(S) : William F. McKay Page 1 of 1

It is certified that error appears in the above-identified patent and that said Letters Patent is hereby corrected as shown below:

In the Specification

In Column 1, Line 6, delete "DEVICE"." and insert -- DEVICE", now Pat. No. 9,730,801. --, therefor.

In Column 9, Line 9, delete "neat" and insert -- near --, therefor.

In Column 10, Line 37, delete "device." and insert -- device). --, therefor.

In Column 14, Line 14, delete "(MW)." and insert -- (MWF). --, therefor.

In Column 16, Line 47, delete "(IFO);" and insert -- (OIF); --, therefor.

In Column 16, Line 53, delete "factor" and insert -- factor-β --, therefor.

Signed and Sealed this
Fourth Day of February, 2020

Andrei Iancu
*Director of the United States Patent and Trademark Office*